United States Patent [19]
Crabbe

[11] 3,931,297
[45] Jan. 6, 1976

[54] 10-HYDROXY PGC COMPOUNDS
[75] Inventor: Pierre Crabbe, Mexico City, Mexico
[73] Assignee: Syntex (U.S.A.) Inc., Palo Alto, Calif.
[22] Filed: Sept. 8, 1972
[21] Appl. No.: 287,249

Related U.S. Application Data
[63] Continuation-in-part of Ser. No. 204,772, Dec. 3, 1971, abandoned.

[52] U.S. Cl.... 260/514 D; 260/240 R; 260/243.6 S; 260/345.7; 260/345.8; 260/340.5; 260/343.3; 260/347.3; 260/347.4; 260/410; 260/448 R; 260/468 R; 260/468 D; 260/468.6; 260/464; 260/473 G; 260/476 R; 260/484 R; 260/485 L; 260/486 R; 260/487; 260/488 R; 260/501.1; 260/501.11; 260/501.17; 424/305; 424/317
[51] Int. Cl.² ................. C07C 61/38; C07C 64/74
[58] Field of Search ............... 260/468 D, 514 D

[56] References Cited
UNITED STATES PATENTS
3,846,475   11/1974   Crabbe et al. .................. 260/468

Primary Examiner—Robert Gerstl
Attorney, Agent, or Firm—Gerard A. Blaufarb; Lawrence S. Squires; William B. Walker

[57] ABSTRACT

10α-Hydroxy-11-desoxy-prostaglandin analogs of the $PGE_1$ and $PGE_2$ and $PGF_1$ α and $PGF_2$ α series, the 11-dehydro derivatives thereof as well as the 9,10-ketals in the PGF series, and methods of preparing same, 9-keto-10α,15α-dihydroxyprosta-13-trans-enoic or 5-cis,13-trans-dienoic acid, 9α,10α,15α-trihydroxyprosta-11,13-trans-dienoic or 5-cis, 11,13-trans-trienoic acid and 9α,10α-isopropyli-denedioxy-15α-hydroxyprosta-13-trans-enoic or 5-cis,13-trans-dienoic acid are representative of the class. Also included are the corresponding pharmaceutically acceptable, non-toxic esters, ethers and salts. These compounds possess prostaglandin-like activity and thus are useful in the treatment of mammals, where prostaglandins are indicated.

3 Claims, No Drawings

10-HYDROXY PGC COMPOUNDS

This application is a continuation-in-part of application Ser. No. 204,772 filed Dec. 3, 1971 now abandoned.

The present invention relates to certain novel prostaglandin derivatives, to a process for the production thereof and to certain novel intermediates obtained by this process.

In a further aspect, the present invention relates to the novel 10α-hydroxy-11-desoxy prostaglandin derivatives of the $PGE_1$, $PGE_2$, $PGF_{1\alpha}$ and $PGF_{2\alpha}$ series, the corresponding 9,10-ketals in the PGF series, as well as the 11-dehydro derivatives thereof, and the corresponding pharmaceutically acceptable, non-toxic esters, ethers and salts.

Prostaglandins are members of a new hormonal system with a remarkable range of biological and pharmaceutical properties. These compounds belong to a group of chemically related 20-carbon chain hydroxy fatty acids containing a five membered ring in the structure and different degrees of unsaturation, a number of which have been reported in the literature. For a review on prostaglandins and the definition of primary prostaglandins, see for example S. Bergströms, Recent Progress in Hormone Research, 22, pp. 153–175 (1966) and Science, 157, page 382 (1967) by the same author.

Prostaglandins are widely distributed in mammalian tissues and have been isolated from natural sources in very small amounts. In addition, a number of the natural occurring prostaglandins have been prepared by chemical synthesis; note for example, J. Am. Chem. Soc., 91, page 5675 (1969); J. Am. Chem. Soc., 92, page 2586 (1970) and J. Am Chem. Soc., 93, pages 1489–1493 (1971) and references cited therein, W. P. Schneider et al., J. Am. Chem. Soc., 90, page 5895 (1968); U. Axen et al., Chem. Commun., page 303 (1969) and W. P. Schneider, Chem. Commun., page 304 (1969).

Because of the remarkable range of biological and pharmacological properties exhibited by this family of compounds, a great deal of interest has focused upon such compounds, and the preparation of analogs of such compounds; accordingly, we have discovered processes and intermediates for preparing modified prostaglandins and derivatives thereof.

The novel prostaglandin derivatives of the present invention can be represented by the following formulas:

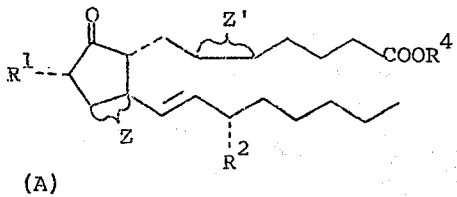

(A)

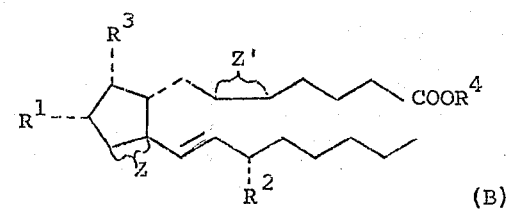

(B)

wherein each of $R^1$, $R^2$ and $R^3$ represent hydroxy or a conventionally hydrolyzable ester or ether thereof; $R^1$ and $R^3$ taken together represent the group

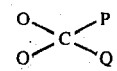

in which each of P and Q is a lower alkyl group or a lower aryl group, or taken together with the carbon atom to which they are attached represent a cyclohexanonide group; $R^4$ represents hydrogen, a lower alkyl group or the pharmaceutically acceptable non-toxic salts of compounds in which $R^4$ is hydrogen, Z represents a carbon-carbon double bond or a saturated linkage; and Z' represents a cis carbon-carbon double bond or a saturated linkage.

The dotted lines shown in the above formulas and in the formulas below indicate that the substituents are in α configuration, i.e. below the plane of the cyclopentane ring.

The double bonds in the compounds of the present invention have the same configuration as in natural prostaglandins of the $PGE_1$, $PGE_2$, $PGF_{1\alpha}$ or $PGF_{2\alpha}$ series, i.e. the double bond at C-5,6 is in cis configuration and the double bond at C-13,14 is in trans configuration.

These novel compounds possess asymmetric centers and thus can be produced as racemic mixtures. The racemic mixtures can be resolved if desired, at appropriate stages by methods known to the skilled in the art, to obtain the respective individual (d) and (l) isomers. It is to be understood that the individual optical isomers as well as mixtures of such isomers are encompassed within the scope of the present invention.

As used herein above and below, the following terms have the following meanings unless expressly stated to the contrary. The term "lower alkyl" refers to a lower alkyl group containing one to six carbon atoms and includes straight and branched chain groups and cyclic alkyl groups, for example, methyl, ethyl, n-propyl, isopropyl, n-butyl, isobutyl, sec-butyl, t-butyl, n-pentyl, isopentyl, sec-pentyl, t-pentyl, cyclopropyl, cyclobutyl, cyclopentyl and the like.

The term "lower aryl" refers to aromatic groups of from 6 to 8 carbon atoms inclusive, e.g. phenyl and benzyl.

The term "conventionally hydrolyzable esters or ethers", are used herein, refers to those physiologically acceptable hydrolyzable ester and ether groups employed in the pharmaceutical art which do not significantly adversely affect the pharmaceutical properties of the parent compound. The conventionally hydrolyzable esters are derived from hydrocarbon carboxylic acids. The term "hydrocarbon carboxylic acid" defines both substituted and unsubstituted hydrocarbon carboxylic acids. These acids can be completed saturated or possess varying degrees of unsaturation (including aromatic), can be of straight chain, branched chain, or cyclic structure, and preferably contain from 1 to 12 carbon atoms. In addition, they can be substituted by functional groups, for example, hydroxy, alkoxy containing up to 6 carbon atoms, acyloxy containing up to 12 carbon atoms, nitro, amino, halogeno, and the like, attached to the hydrocarbon backbone chain. Typical conventional hydrolyzable esters thus included within the scope of the term and the instant invention are acetate, propionate, butyrate, valerate, caproate, enanthate, caprylate, perlargonate, acrylate, undecenoate, phenoxyacetate, benzoate, phenylacetate, diphenylacetate, diethylacelate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemiβ,β-dimethylglutarate, acetoxyacetate, 2-chloro-4-nitro-benzoate, aminoacetate, diethylaminoacetate, piperidinoacetate, β-chloropropionate, trichloroacetate, β-chlorobutyrate, bicyclo-[2.2.2]-octane-1-carboxylate, 4-methylbutylo-[2.2.2]-oct-2-ene-1-carboxylate, and the like. The preferred conventional hydrolyzable ester is acetate.

"Conventional hydrolyzable ethers" include the methyl, ethyl, cyclopentyl, tetrahydrofuran-2-yl, tetrahydropyran-2-yl, and 4-methoxytetrahydropyran-4-yl ethers.

The addition salts are derived from pharmaceutically acceptable basic salts, including metal salts such as sodium, potassium, calcium, magnesium, aluminum and the like, as well as organic amine salts such as ammonium, triethylamine, 2-dimethylamino ethanol, 2-diethylamino ethanol, lysine, arginine, caffeine, procaine, N-ethylpiperidine, hydrabamine and the like. The term pharmaceutically acceptable refers to salts which do not significantly adversely affect the properties of the parent compound.

The novel prostaglandin derivatives of the $PGE_2$ and $PGF_{2\alpha}$ series of the invention can be obtained by the following schematically illustrated process sequence:

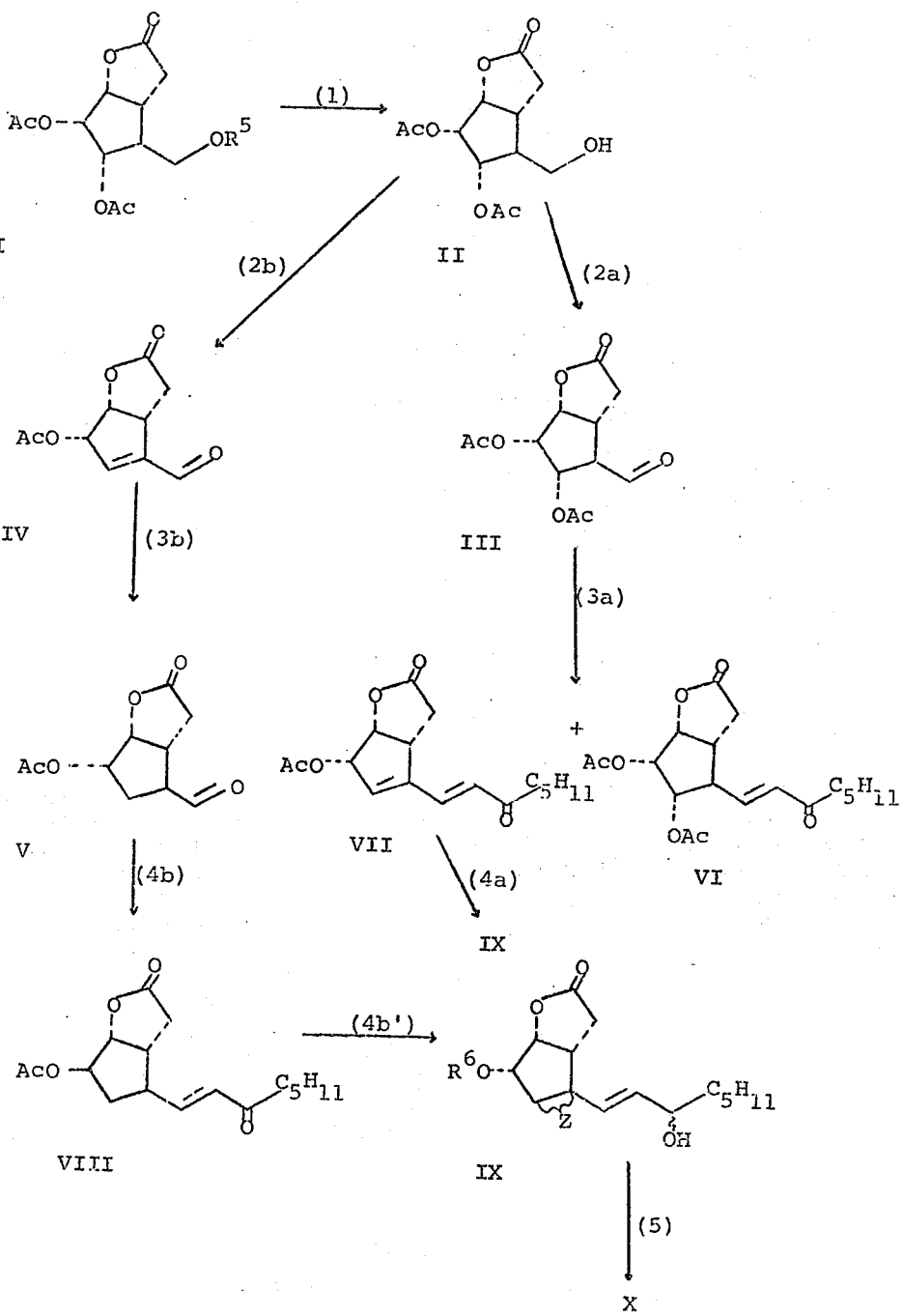

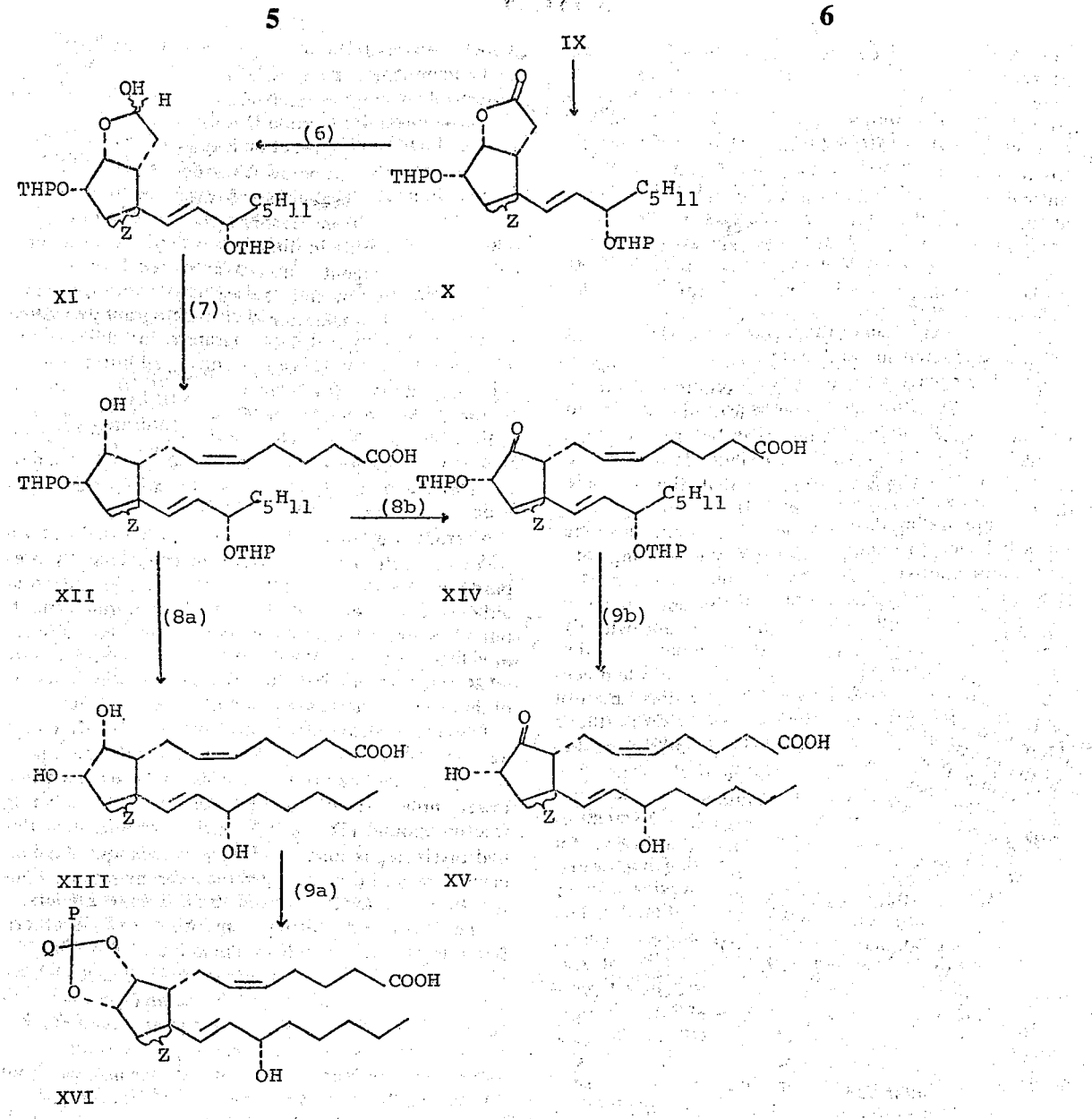

wherein Ac is acetyl or other conventional hydrolyzable acyl group; $R^5$ represents methyl or benzyl or equivalent group; $R^6$ represents hydrogen or acetyl; Z, P and Q have the above indicated meaning; and THP represents tetrahydropyran-2'-yl.

The wavy lines ( ⌇ ) indicate the α or β configuration, or mixtures thereof.

In practicing the process illustrated above, the starting compounds of formula I, namely (2'α-hydroxy-3'α,4'α-diacetoxy-5'β-benzyloxymethylcyclopent-1'α-yl)-acetic acid 1,2'-lactone or (2'α-hydroxy-3'α,4'α-diacetoxy-5'β-methoxymethylcyclopent-1'α-yl)-acetic acid 1,2'-lactone are cleaved under the appropriate conditions, to yield the 5'β-hydroxymethyl compound of formula II.

Compound I ($R^5$ = benzyl) can be cleaved by hydrogenolysis in the presence of a metal catalyst of group VIII of the Periodic Table, such as palladium, platinum or nickel, and preferably in the presence of a catalytic amount of perchloric acid, to produce the hydroxymethyl compound of formula II. This hydrogenolysis is preferably conducted in a suitable inert organic solvent such as dimethoxyethane, acetone, ethyl acetate, methanol, and the like conveniently at about room temperature and atmospheric pressure or higher, until the absorption of hydrogen ceases. In the preferred embodiments the hydrogenolysis is effected using palladium charcoal as catalyst and dimethoxyethane as solvent.

Compound I ($R^5$ = methyl) can be converted into the hydroxymethyl compound of formula II by cleavage with boron tribromide in methylene chloride, at temperatures of about between −78° to 0°C, for a period of time of about 1 hour. The product is isolated from the reaction mixture by destruction of the excess boron tribromide followed by neutralization with base and extraction with an adequate organic solvent immiscible with water, e.g. methylene chloride or ethyl acetate; the product can be further purified by chromatography.

The foregoing hydroxymethyl compound (II) can then be oxidized (step 2a) to the corresponding formyl derivative, the compound of formula III. Suitable oxidants are, for example, chromium trioxide-pyridine complex, chromium trioxide-dipyridine complex (Collins' reagent) or dicyclohexylcarbodiimide or diisopropylcarbodiimide in dimethylsulfoxide (Moffatt's reagent); best results are obtained using chromium trioxidedipyridine complex, prepared as described by J. C. Collins et al., in Tetrahedron Letters, 3363 (1968). Isolation of the aldehyde compound can be accomplished by conventional procedures, however, acid or alkaline conditions should be avoided. This aldehyde compound is unstable in air and therefore it is recommended to perform the next step of the process in the crude compound.

When the oxidation of the hydroxymethyl compound (II) is conducted in the presence of an acid or base (step 2b) or when an acid or base is added during the isolation procedure, dehydroacetoxylation occurs to yield the unsaturated aldehyde of formula IV.

The compounds of formula V can be prepared (step 3b) by hydrogenating the unsaturated aldehyde (IV) in the presence of a catalyst such as a palladium-charcoal catalyst, in a suitable inert organic solvent, e.g. using ethyl acetate or dimethoxyethane as solvent. This reaction is believed to occur via the corresponding saturated monoacetoxy aldehyde having the aldehyde group in $\alpha$ configuration, which then spontaneously isomerizes into compound V (the compound with the more stable configuration).

Step 3a can be effected by reacting the crude diacetoxy aldehyde of formula III with the sodium anion of dimethyl 2-oxoheptylphosphonate in dimethoxyethane yielding a mixture of the trans enone and dienone lactones of formulas VI and VII, respectively, which can be separated by conventional techniques. This transformation involves a modified Wittig reaction. Procedures for the Wittig reaction are well known in the art, see for example, S. Trippet et al., Adv. in Organic Chemistry, Vol. 1, pp. 83–102, S. Trippet, Quarterly Reviews, Vol. 17, pp. 400–440. The sodium anion of dimethyl 2-oxoheptylphosphonate can be prepared in accordance with the method described by E. J. Corey et. al., J. Am. Chem. Soc., 88, 5654 (1966). The reaction is conducted under an inert atmosphere, i.e under nitrogen or argon atmosphere, at temperatures between 0° and 40°C, preferably at room temperature or below, using at least one molar equivalent of the reagent per mol of aldehyde, and preferably 1.2 to 2 moles. This reaction is carried out for a period of about from 1 to 4 hours, depending on the temperature and concentration of the reaction mixture. In the preferred conditions, the reaction is conducted at room temperature for two hours or less, as longer reaction times give rise to more elimination products. The reaction product can be recovered from the reaction mixture by neutralization of the excess base with acetic acid to pH 7, followed by evaporation of the solvent under high vacuum, at low temperature, or by adding water and extracting the reaction product with an adequate solvent immiscible with water, e.g. methylene chloride, diethyl ether and the like, followed by evaporation of the solvent. Compounds VI and VII can be separated by conventional techniques, such as chromatography on silica gel or thin-layer chromatography.

In step 4b the above-described alkylation reaction is performed in the same manner using the saturated aldehyde of formula V yielding the enone lactone of formula VIII.

The dienone lactone of formula VII and the enone lactone of formula VIII can be conveniently selectively reduced (steps 4a and 4b, respectively) with a solution of zinc borohydride in an ether solvent such as dimethoxyethane, to yield a mixture of the 15$\alpha$-hydroxy lactones and their 15$\beta$ epimers (R and S isomers, ratio ca 1:1) compounds of formula IX ($R^6$ = acetyl, Z = single or double bond). The reaction is typically conducted at room temperature or below for about from 15 minutes to several hours. The zinc borohydride reagent solution can be prepared from freshly fused zinc chloride and sodium borohydride in dimethoxyethane. Typically an excess of the reagent is used for this reduction.

The epimeric 15$\alpha$ and 15$\beta$ hydroxy compounds can be separated by conventional chromatography on silica gel or by thin-layer chromatography. In addition, the 15$\beta$-epimer byproduct can be converted into the starting compounds of formulas VII or VIII by well known methods for the obtention of $\alpha,\beta$-unsaturated ketones from allylic alcohols such as, for example, by reaction with manganese dioxide in methylene chloride or chloroform or with 2,3-dichloro-5,6-dicyano-1,4-benzoquinone in dioxane.

Alternatively, this reduction can be carried out via treatment with a borohydride ion (conveniently prepared by reaction of a trialkylborane derived from either racemic or (+)-limonene, hexylborane and t-butyl lithium, in the presence of hexamethylphosphoramide at about −130° to −100°C, and preferably −120°C). In this case the 15$\alpha$-alcohol predominates, obtaining only small amounts of the 15$\beta$-epimer.

The 15$\alpha$-hydroxy compounds of formula IX ($R^6$ = acetyl) can then be saponified under alkaline conditions using an alkali metal hydroxide or carbonate in a lower aliphatic alcohol, to produce the corresponding free compound (IX, $R^6$ = hydrogen). Preferably, this hydrolysis step is conducted using anhydrous potassium carbonate and conducting the reaction at room temperature or below, for about 30 minutes to 2 hours.

The 10$\alpha$,15$\alpha$-dihydroxy compounds can be etherified (step 5) with dihydropyran in methylene chloride, in the presence of catalytic amounts of an acid catalyst, e.g. p-toluenesulfonic acid, under anhydrous conditions, to produce the bistetrahydropyranyloxy derivatives of formula X. The reaction is typically conducted at room temperature for about 15 minutes using about 3 molar equivalents of dihydropyran in an inert organic solvent, e.g. methylene chloride. A larger excess of dihydropyran, or longer reaction periods are undesirable as they produce polymerization of this reagent.

The product can be conveniently isolated by adding a few drops of pyridine to the product reaction mixture followed by conventional extraction and evaporation of the organic extract, at low temperature.

In step 6, the bistetrahydropyranyloxy-lactones of formula X are reduced to the corresponding isomeric lactols of formula XI. This can be conveniently effected via treatment with 1.1 to 3 molar equivalents of diisobutylaluminum hydride in a suitable organic solvent. The treatment is typically conducted at about from −30° to −70°C, preferably at about −60°C, for a period of about from 10 to 30 minutes, preferably using about 2 molar equivalents of diisobutylaluminum hydride per mole equivalent of the compound of formula X. Suitable organic solvents for this reaction are the aromatic hydrocarbons such as toluene or xylene.

The product can be isolated from the reaction mixture by conventional separation procedures and can be used for the next step without separation of the isomers.

Step 7 can be conveniently effected by condensation of the crude lactols of formula XI with a Wittig reagent derived form 5-triphenylphosphoniopentanoic acid and sodium methylsulfinyl carbanion in dimethylsulfoxide solution. This condensation yields the corresponding compounds of formula XII, namely 9α-hydroxy-10α, 15α-bistetrahydropyranyloxyprosta-5-cis,11,13-trans-trienoic acid (10,15-bistetrahydropyranylether of 10α-hydroxy-11-desoxy-11-dehydro-PGF$_{2\alpha}$), (XII, Z = double bond) or 9α-hydroxy-10α,15α-bistetrahydropyranyloxyprosta-5-cis, 13-trans-dienoic acid (10,15-bistetrahydropyranylether of 10α-hydroxy-11-desoxy-PGF$_{2\alpha}$), (XII, Z = saturated linkage).

This reaction is typically conducted at about room temperature for about from 2 to 24 hours under anhydrous conditions. Conveniently the reaction is followed by thin-layer chromatography and discontinued when substantially completed. This reaction is preferably carried out under an inert atmosphere, i.e. under argon or nitrogen atmosphere. The initial product is obtained as the sodium salt soluble in water. The free acid can be liberated by acidification with oxalic acid or another weak acid to pH 2, followed by conventional extraction and evaporation. The prostaglandin derivative is further purified by thin-layer chromatography.

The 5-triphenyphosphoniopentanoic acid can be prepared as described by R. Greenwald et al., in J. Org. Chem., 28, 1128 (1963), from 5-bromopentanoic acid and triphenylphosphine in acetonitrile. The sodium methylsulfinyl carbanion is obtained from sodium hydride and dimethylsulfoxide, stirring the mixture at about 75°C until the evolution of gas ceases. Generally, it is recommended to prepare these reagents just prior to the reaction with the lactols of formula XI.

Typically a molar excess of reagents is used relative to the lactol starting material (formula XI). Preferably the triphenylphosphoniopentanoic acid is used in amounts varying from about 2 to 5.0 moles per mole of starting lactol (formula XI) while the amounts of sodium methylsulfinyl carbanion vary between about 2 to about 10 moles. Best results are obtained using 2.5 molar equivalents of the acid reagent and 5 molar equivalents of the anion per mole of lactol (formula XI).

The tetrahydropyranyloxy functions in compounds of formula XII can be hydrolyzed (step 8a) under mild acidic conditions, e.g. using a weak acid such as acetic acid, oxalic acid, tartaric acid and the like in the presence of water, to produce the free hydroxy compounds of formula XIII, i.e. 10α-hydroxy-11-desoxy-11-dehydro-PGF$_{2\alpha}$, (XIII, Z = double bond) or 10α-hydroxy-11-desoxy-PGF$_{2\alpha}$ (XIII, Z = saturated linkage). The bistetrahydropyranyloxy compound is preferably dissolved in an inert organic solvent miscible with water, e.g. tetrahydrofuran, dioxane and like. This hydrolysis is preferably conducted using aqueous acetic acid, at a temperature comprised between 0° and 50°C for about from 4 to 10 hours, depending upon the temperature used. The preferred concentration of aqueous acetic acid is 65:35, however, other concentrations are also practical.

Step 8b can be conveniently effected by the oxidation of the compounds of formula XII with Jones' reagent (J. Chem. Soc., page 2631 (1970)). Moffatt's reagent (J. Am. Chem. Soc., Vol. 87, page 5670 (1965)) or with aqueous chromic acid in diethyl ether (H. C. Brown et al., J.O.C., 36, 387 (1971)). The 9-keto-products of formula XIV, namely 9-keto-10α,15α-bistetrahydropyranyloxyprosta-5-cis,11,13-trans-trienoic acid (XIV, Z = double bond) or 9-keto-10α,15α-bistetrahydropyranyloxyprosta-5-cis,13-trans-dienoic acid (XIV, Z = saturated linkage) can be hydrolyzed (step 9b) via treatment mild acidic conditions as described herein before, to afford respectively 10α-hydroxy-11-desoxy-11-dehydro-PGE$_2$ (XV, Z = double bond) or 10α-hydroxy-11-desoxy PGE$_2$. (XV, Z = saturated linkage).

Step 9a can be conveniently effected by condensing the 10α-hydroxy-11-desoxy-PGF$_{2\alpha}$ or the 11-dehydro derivative, compounds of formula XV with a ketone in the presence of an acid catalyst, preferably using p-toluenesulfonic acid as catalyst produces the corresponding ketal of formula XVI. In this reaction the ketone used can serve as both reagent and solvent, or alternatively the reaction can be carried out in the presence of a cosolvent. Examples of suitable ketones used are acetone, methylethyl ketone, diethyl ketone, acetophenone, cyclohexanone and the like. The reaction is preferably conducted in the presence of an organic solvent inert to the reaction, such as tetrahydrofuran, dioxane or 2,2-dimethoxypropane, at room temperature for about from 1 to 5 hours. The ketal is isolated by adding a few drops of pyridine to the reaction mixture, followed by evaporation to dryness and purification by conventional techniques.

The PGE$_1$ and PGF$_{1\alpha}$ series of compounds of formula A and B, of the invention, can be conveniently prepared by selectively reducing the C-5(6)-cis-olefin bond of the corresponding PGE$_2$ or PGF$_{2\alpha}$ series of derivatives of formulas A and B, of the invention, according to the same procedure as described by Koch et al. in the Journal of Labelled Compounds, Vol. VI, No. 4, page 395 (October–December, 1970) with respect to the reduction of PGE$_2$ prostaglandins to PGE$_1$ prostaglandins.

The hydroxyl groups in the novel prostaglandin derivatives of formulas XII, XIII, XV and XVI can be esterified or etherified in a conventional manner to produce mono-, di-, or triesters or mono-, di-, or triethers, depending upon the particular prostaglandin derivative. For example, esterification can be accomplished by reaction of the hydroxylated compound with a carboxylic acid anhydride or chloride of less than 12 carbon atoms in pyridine solution.

Etherification can also be carried out by conventional techniques. Thus, reaction with dihydropyran, dihydrofuran or 4-methoxy-5,6-dihydro-2H-pyran in an inert solvent such as benzene or methylene chloride and in the presence of an acid catalyst produces the tetrahydropyran-2'-yloxy, tetrahydrofuran-2'-yloxy or 4'-methoxy-tetrahydropyran-4'-yloxy derivatives, respectively. Methyl, ethyl and cyclopentyl ethers, for example, are prepared upon reaction of the hydroxylated compound with sodium hydride and methyl iodide; ethyl iodide and cyclopentyl bromide, respectively.

Although the esterification or etherification reactions are usually effected using an excess of the esterifying or etherifying agents, it is preferable to use at least one molar equivalent of said reagents per hydroxyl group present in the starting compound.

The salt derivatives of the prostadienoic and prostatrienoic acids of the present invention can be prepared by treating the corresponding free acids with about one molar equivalent of a pharmaceutically acceptable base. Representative pharmaceutically acceptable bases are sodium hydroxide, potassium hydroxide, ammonium hydroxide, calcium hydroxide, trimethylamine, triethylamine, tripropylamine, β-(dimethylamino) ethanol, β-(diethylamino) ethanol, arginine, lysine, caffeine, procaine and the like. The reaction is conducted in an aqueous solution, alone or in combination with an inert water miscible organic solvent, at a temperature of from about 0° to about 30°C, preferably at room temperature. Typical inert, water miscible organic solvents include methanol, ethanol, isopropanol, butanol, dioxane and tetrahydrofuran. When divalent metal salts are prepared, such as the calcium salts or magnesium salts, the free acid starting material is treated with at least one half molar equivalent of the pharmaceutically acceptable base.

The alkyl esters can be obtained by treatment of the free acid with an excess of a diazoalkane such as diazomethane, diazoethane or diazopropane in ether or methylene chloride solution, in a conventional manner.

In conducting the aforedescribed processes, it is generally preferred to separate or isolate the respective products of each reaction step prior to their use as starting materials in subsequent steps. Illustrative nonlimiting separation and isolation procedures can be had by reference to the appropriate Examples set forth herein below. Also where pure optical isomer products are desired, such products can be obtained by the use of pure optical isomer starting materials or by resolution of the racemic product (or starting materials) according to conventional procedures such as, for example, described by Corey et al., J. Am. Chem. Soc., 92, 397 (1970).

Also although the above processes, for purposes of simplicity have been described with respect to tetrahydropyranyl and acetate protecting groups, other conventional suitable ether and ester protecting groups could, of course, also be used.

The compounds of formula I used as starting materials in the above described process are prepared in accordance with the methods described, for example, by E. J. Corey et al., in J. Am. Chem. Soc., 91, 5675 (1969); J. Am. Chem. Soc., 92, 1397 (1970); J. Am. Chem. Soc., 93, pages 1489, 1490 and 1491 (1971) and references cited therein, followed by deiodination with silver acetate, as described in copending application Serial No. 204,681 filed December 3, 1971 and conventional esterification, as illustrated by the following sequence of reactions:

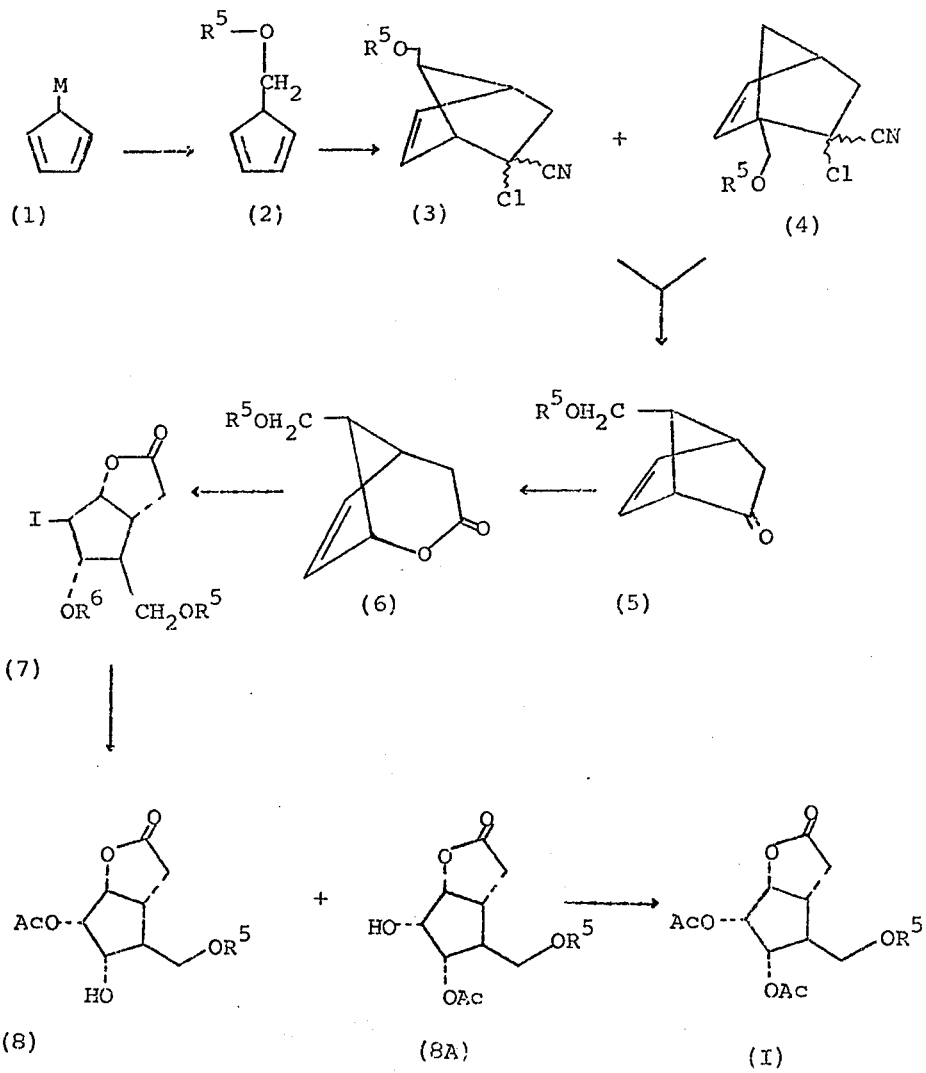

wherein $R^5$ and $R^6$ have the above indicated meaning; and M represents sodium or thallium.

Briefly, this method comprises the reaction of cyclopentadienylsodium or cyclopentadienylthallium (1), obtained by reaction of cyclopentadiene with sodium hydride or aqueous thallous sulfate in the presence of potassium hydroxide (E. J. Corey et al., J. Am. Chem. Soc., 93, page 1489 (1971), with a slight excess of chloromethyl methylether or chloromethylbenzyl ether in tetrahydrofuran at approximately -55°C, to yield respectively the 5-methoxymethyl-1,3-cyclopentadiene 2, ($R^5$ = methyl) or 5-benzyloxymethyl-1,3-cyclopentadiene 2 ($R^5$ = benzyl) which are subjected to the Diels Alder reaction with an excess (about five molar equivalents) of 2-chloro-acrylonitrile in the presence of cupric fluoroborate as catalyst to yield a mixture of the endo-exo cyano nitriles of formulas (3) and (4) ($R^5$ = methyl or benzyl, respectively). This mixture of stereoisomeric nitriles is treated with potassium hydroxide in dimethylsulfoxide to yield the anti-bicyclic ketones of formula (5), i.e. 7-syn-methoxymethyl-2-norbornen-5-one ($R^5$ = methyl) or 7-syn-benzyloxymethyl-2-norbornen-5-one ($R^5$ = benzyl), respectively, which upon reaction with a slight molar excess of m-chloro-perbenzoic acid in methylene chloride in the presence of sodium bicarbonate result in selective Bayer-Villiger oxidation to form the corresponding lactone (6), namely 2-oxa-3-oxo-$\Delta^5$-8-syn-methoxymethylbicyclo (3.2.1)-octane ($R^5$ = methyl) and 2-oxa-3-oxo-$\Delta^5$-8-syn-benzyloxymethylbicyclo (3.2.1)-octane ($R^5$ = benzyl). Saponification of the foregoing lactones of formula (6) with 2.5 equivalents of sodium hydroxide in aqueous methanol, followed by neutralization with carbon dioxide and treatment with 2.5 equivalents of aqueous potassium triiodide solution at 0° to 5°C produce the respective hydroxy-iodolactones of formula (7), namely (2'$\alpha$,4'$\alpha$-dihydroxy-3'$\beta$-iodo-5'$\beta$-methoxymethylcyclopent-1'$\alpha$-yl)-acetic acid 1,2'-lactone ($R^5$ = methyl, $R^6$ = H) and (2'$\alpha$,4'$\alpha$-dihydroxy-3'$\beta$-iodo-5'$\beta$-benzyloxymethylcyclopent-1'$\alpha$-yl)-acetic acid 1,2'-lactone ($R^5$ = benzyl, $R^6$ = H), which are esterified with acetic anhydride in pyridine, under conventional conditions to yield the corresponding acetoxy compounds (7, $R^6$ = acetyl). Upon reaction of the iodo lactones with 1 to 4 molar equivalents of silver acetate in aqueous acetic acid, at reflux temperature for about 2 hours, there is obtained a mixture of hydroxyacetates (8 and 8A) which is converted into the fully esterified compound by conventional treatment with acetic anhydride in pyridine solution, thus obtaining the desired (2'$\alpha$-hydroxy-3'$\alpha$,4'$\alpha$-diacetoxy-5'$\beta$-methoxymethylcyclopent-1'$\alpha$-yl)-acetic acid 1,2'-lactone or (2'$\alpha$-hydroxy-3'$\alpha$,4'$\alpha$-diacetoxy-5'$\beta$-benzyloxymethylcyclopent-1'$\alpha$-yl)-acetic acid 1,2'-lactone, the compounds of formula I.

The compounds, esters and salts of the invention exhibit prostaglandin-like biological activities and thus are useful in the treatment of mammals where the use of prostaglandins are indicated. The compounds, esters and salts of the invention are bronchodilators and thus are useful in treating mammals for bronchial spasm or wherever strong bronchodilators are indicated. These compounds are also useful in controlling or palliating hypertension in mammals and further exhibit central nervous system depressant activity in mammals, and are useful as sedatives. In addition, the compounds are useful for inducing labor, in pregnancy, and for inducing menses to correct or reduce menstrual abnormalities.

The compounds and/or salts, of the invention, can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate aand pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds and/or salts can, for example, be administered as an aerosol comprising the compounds or salts in an inert propellant together with a cosolvent (e.g. ethanol) together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.1 to 10 mg. per kg. of body weight. The precise effective dosage will, of course, vary depending upon the mode of administration, condition being treated and host.

The following Preparations and Examples illustrate the invention, but are not intended to limit its scope. Also unless expressly stated to the contrary, racemic mixtures are used as starting materials, and correspondingly, racemic mixtures are obtained as products. The abbreviation t.l.c refers to thin-layer chromatography and all mixture ratios used with regard to liquids refer to volume ratios. Also, where necessary, preparations and examples are repeated to provide sufficient starting material for subsequent examples.

PREPARATION 1

A. To a stirred solution of 125 g. of thallium sulfate and 50 g. of potassium hydroxide in 750 ml. of water are added, under an atmosphere of argon, 43 ml. of freshly distilled cycyclopentadiene and the mixture is vigorously stirred for ten minutes; the yellow precipitate formed is filtered off, washed with ice water, methanol and ether, to yield 132 g. of cyclopentadienylthallium.

B. A mixture of 216.28 g. of benzyl alcohol, 61.44 g. of paraformaldehyde, 481.6 g. of anhydrous magnesium sulfate and 1200 ml. of methylene chloride is cooled to a temperature of between −50° to −55°C in a dry ice-acetonitrile bath, and the stirred cold solution is saturated with anhydrous hydrogen chloride gas. The reaction mixture is kept at −50° to −55°C for 10 minutes further, and then excess of hydrogen chloride is eliminated by passing a stream of nitrogen during 30 minutes. The reaction mixture is filtered and the solid material washed well with pentane, and the combined filtrates are evaporated to dryness at a temperature below 30°C, to produce an oil which is distilled under reduced pressure to yield chloromethyl benzyl ether.

C. A suspension of 132 g. of cyclopentadienyl thallium in 200 ml. of anhydrous ether is cooled to −20°C in a dry ice-carbon tetrachloride bath. To the cooled mixture are added under stirring and under an argon atmosphere, in a 15 minute period, 90 g. of chloromethyl benzyl ether. The reaction mixture is stirred for 3½ hours at −20°C, it is then filtered in a filtration flask previously cooled to −78°C and the solid precipitate washed with cold pentane (−78°C).

The filtered solution is immediately added to a mixture of 216 g. of anhydrous -chloroacrylonitrile and 30 g. of anhydrous cupric fluoroborate, previously cooled to −78°C. The reaction mixture is evaporated to half its original volume at a temperature not higher than 0°C, and the concentrate is stirred at 0°C for 48 hours. The reaction mixture is then poured into 200 ml. of saturated sodium chloride solution and extracted three times with ether. The combined extracts are washed with saturated sodium bicarbonate solution (2 × 200 ml.), and saturated sodium chloride solution (2 × 200 ml.), dried over magnesium sulfate and evaporated to dryness under reduced pressure. The resulting residue is purified by filtration through 100 g. of silica gel using benzene as eluant, thus obtaining the pure 2-chloro-2-cyano-$\Delta^5$-7-syn-benzyloxymethylbicyclo-(2.2.1)-heptane.

PREPARATION 2

To a well-stirred slurry of 74.1 g. of cyclopentadienylthallium in 100 ml. of anhydrous ether cooled to −20° to −22°C (internal temperature) in a dry ice-carbon tetrachloride bath under an argon atmosphere, are added dropwise, in a 15 minute period, 20.13 g. of chloromethyl methyl ether and the slurry is stirred at −20° to −22°C for 7 hours. The reaction mixture is then filtered into a precooled (−70°C, dry ice-acetone) flask and the residue of thallium chloride washed with three 100 ml. portions of cold (−70°C) ether. The combined filtrate is added dropwise from a dropping funnel with a dry-ice jacket to a suspension of 29.65 g. of cupric tetrafluoroborate in 87.5 g. of anhydrous α-chloroacrylonitrile maintained at 0°C. When the addition is complete, the mixture is stirred at 0°C in the dark for 18 hours. One hundred milliliters of saturated sodium chloride solution are then added and the reaction mixture extracted with ether. The ether extracts are successively washed with saturated sodium bicarbonate (2 × 100 ml.) and sodium chloride (2 × 100 ml.), and dried over magnesium sulfate. Evaporation of the solvent under reduced pressure at room temperature gives 2-chloro-2-cyano-$\Delta^5$-7-syn-methoxymethylbicyclo-(2.2.1)-heptane as a clear pale yellow oil.

PREPARATION 3

To a stirred solution of 100 g. of 2-chloro-2-cyano-$\Delta^5$-7-syn-benzyloxymethylbicyclo-(2.2.1)-heptane in 386 ml. of dimethylsulfoxide is added dropwise, in a 15 minute period and under an argon atmosphere, a hot solution of 105.2 g. of potassium hydroxide in 52.6 ml. of water. The reaction mixture is stirred for 28 hours at room temperature, diluted to twice its volume with ice water and extracted several times with ether. The combined organic extract is washed twice with saturated sodium carbonate solution, dried over magnesium sulfate and evaporated to dryness. The residue is purified by distillation under high vacuum (0.6 mm.) to yield 7-syn-benzyloxymethyl-2-norbornen-5-one, homogeneous on t.l.c.

By the same procedure but using 2-chloro-2-cyano-$\Delta^5$-7-syn-methoxymethylbicyclo-(2.2.1)-heptane in lieu of 2-chloro-2-cyano-$\Delta^5$-7-syn-benzyloxymethylbicyclo-(2.2.1)-heptane there is obtained 7-syn-methoxymethyl-2-norbornen-5-one.

PREPARATION 4

To a suspension of 55 g. of m-chloroperbenzoic acid and 43.5 g. of sodium bicarbonate in 570 ml. of anhydrous methylene chloride are added 57 g. of 7-syn-benzyloxymethyl-2-norbornen-5-one, in a 15 minute period and under stirring, maintaining to temperature at about 25°C. The reaction mixture is stirred for three hours further, and diluted with methylene chloride. The resulting mixture is vigorously stirred with 470 ml. of saturated aqueous sodium sulfite solution, the organic layer is separated and washed with saturated sodium sulfite solution. The aqueous phase is extracted with methylene chloride and the combined organic methylene chloride extracts are dried over magnesium sulfate and evaporated to dryness under reduced pressure, thus yielding 2-oxa-3-oxo-$\Delta^5$-8-syn-benzyloxymethylbicycl-3.2.1)-octane as a homogeneous oil.

By the same procedure but using 7-syn-methoxymethyl-2-norbornen-5-one in place of 7-syn-benzyloxymethyl-2-norbornen5-one there is obtained -2-oxa-3-oxo-$\Delta^5$-8-syn-methoxymethylbicyclo-(3.2.1)-octane.

PREPARATION 5

To a solution of 60 g. of 2-oxa-3-oxo-$\Delta^5$-8-syn-benzyloxymethylbicyclo-(3.2.1)-octane in 70 ml. of methanol is added, at 0°C, a solution of 30 g. of sodium hydroxide in 247 ml. of water, and the resulting mixture is stirred at room temperature for 3 hours. The methanol is then evaporated under vacuo at a temperature below 30°C, cooled to 0°C and extracted with ether to eliminate the unsaponifiable products. The aqueous phase is neutralized with carbon dioxide and immediately treated with solution of 188.1 g. of iodine and 369 g. of potassium iodide in 275 ml. of water. The reaction mixture is stirred for 48 hours at 0°C and diluted with sodium sulfite solution until complete decoloration. It is then saturated with sodium potassium tartrate and extracted with methylene chloride. The organic extracts are dried over magnesium sulfate and evaporated to dryness under reduced pressure. The oily residue is crystallized from ether-methylene chloride, to yield the pure (2′α,4′α-dihydroxy-3′β-iodo-5′β-benzyloxymethylcyclopent-1′α-yl)-acetic acid 1,2′-lactone.

By the same procedure, 2-oxa-3-oxo-$\Delta^5$-8-syn-methoxymethylbicyclo-(3.2.1)-octane is converted into (2'α,4'α-dihydroxy-3'β-iodo-5'β-methoxymethylcyclopent-1'α-yl)-acetic acid 1,2'-lactone.

PREPARATION 6

A mixture of 2.5 g. of (2'α,4'α-dihydroxy-3'β-iodo-5'β-benzyloxymethylcyclopent-1'α-yl)-acetic acid 1,2'-lactone, 2.5 ml. of pyridine and 5 ml. of acetic anhydride is kept at room temperature for 30 minutes. The solvents are then evaporated under reduced pressure, and the residue crystallized from ether, to yield (2'α-hydroxy-4'α-acetoxy-3'β-iodo-5'β-benzyloxymethylcyclopent-1'α-yl)-acetic acid 1,2'-lactone.

In a similar manner (2'α,4'α-dihydroxy-3'β-iodo-5'β-methoxymethylcyclopent-1'α-yl)-acetic acid 1,2'-lactone is converted into the corresponding 4'-acetoxy derivative.

PREPARATION 7

To a solution of 2 g. of (2'α-hydroxy-4'α-acetoxy-3'β-iodo-5'β-benzyloxymethylcyclopent-1'α-yl)-acetic acid 1,2'-lactone in 20 ml. of acetic acid are added 1.4 ml. of water and 2 g. of silver acetate, and the mixture is refluxed for 2 hours. The silver iodide is separated by filtration and washed several times with ethyl acetate. The combined organic filtrates are evaporated to dryness under reduced pressure, the residue is diluted with ethyl acetate and the insoluble material filtered off. Upon evaporation of the filtrate under vacuo there is produced a mixture of (2'α,3'α-dihydroxy-4'α-acetoxy-5'β-benzyloxymethylcyclopent-1'α-yl)-acetic acid 1,2'-lactone and (2'α,4'α-dihydroxy-3'α-acetoxy-5'β-benzyloxymethylcyclopent-1'αyl)-acetic acid 1,2'-lactone as an oil, which is converted into (2'α-hydroxy-3'α,4'α-diacetoxy-5'β-benzyloxymethylcyclopent-1'α-yl)-acetic acid 1,2'-lactone by esterification with acetic anhydride in pyridine in accordance with the method of Preparation 6.

In a similar manner but using (2'α-hydroxy-4'α-acetoxy-3'β-iodo-5'β-methoxymethylcyclopent-1'α-yl)-acetic acid 1,2'-lactone as starting material there is obtained (2'α-hydroxy-3'α,4'α-diacetoxy-5'β-methoxymethylcyclopent-1'α-yl)-acetic acid 1,2'-lactone.

EXAMPLE 1

A. To a prehydrogenated suspension of 1 g. of 10% palladium charcoal catalyst in 50 ml. of dimethoxyethane are added 5 g. of (2'α-hydroxy-3'α,4'α-diacetoxy-5'β-benzyloxymethylcyclopent-1'α-yl)-acetic acid 1,2'-lactone and 1.25 ml. of perchloric acid, and the mixture is stirred under hydrogen atmosphere until the absorption of hydrogen ceases. The catalyst is then separated by filtration and washed with ether, and the combined orgainc filtrates are evaporated to dryness under reduced pressure, to yield (2'α-hydroxy-3'α,4'α-diacetoxy-5'β-hydroxymethylcyclopent-1'α-yl)-acetic acid 1,2'-lactone which is purified by thin-layer chromatography using methylene chloride-ethyl acetate (9:1) as eluant.

B. A stirred solution of 15 g. of (2'α-hydroxy-3'α,-4'α-diacetoxy-5'β-methoxymethylcyclopent-1'α-yl)-acetic acid 1,2'-lactone in 190 ml. of anhydrous methylene chloride is cooled to −78°C in a dry ice-acetone bath and treated with 25 ml. of boron tribromide. The stirred mixture is allowed to warm rapidly to 0°C and kept at this temperature for 50 minutes. To the resultant solution are then added 270 ml. of ether to decompose excess boron tribromide maintaining the reaction mixture at 0°C. It is then poured into a vigorously stirred slurry of 95 g. of sodium bicarbonate in 500 ml. of a saturated solution of sodium potassium tartrate; the organic layer is separated and the aqueous phase extracted with methylene chloride. The combined organic extracts are dried over magnesium sulfate and evaporated to dryness under reduced pressure, to afford (2'α-hydroxy-3'α,4'α-diacetoxy-5'β-hydroxymethylcyclopent-1'α-yl)-acetic acid 1,2'-lactone, identical to the obtained in part A.

EXAMPLE 2

A. Preparation of chromium trioxide-dipyridine complex. To 600 ml. of anhydrous pyridine are added under stirring at a temperature of between 10° and 15°C and in a 15 minute period, 80 g. of chromium trioxide, which has been previously dried at 110°C for 48 hours. The reaction mixture is stirred for 30 minutes further and rapidly filtered in the absence of moisture. The solid is washed with anhydrous pentane, dried and stored in a desiccator.

B. To a suspension of 20 g. of diatomaceous earth (dried for 24 hours at 105°C) and 11.8 g. of the chromium trioxidedipyridine complex in 120 ml. of anhydrous methylene chloride, cooled to −5°C are added under stirring 1.3 g. of (2'α-hydroxy-3'α,4'α-diacetoxy-5'β-hydroxymethylcyclopent-1'α-yl)-acetic acid 1,2'-lactone and the mixture is stirred for 10 minutes further, maintaining the temperature between −5° and 0°C; 40 g. of sodium bisulfite monohydrate are then added and the mixture is stirred for an additional 10 minute period, filtered through magnesium sulfate an the solids washed with methylene chloride, receiving the filtrate in a flask cooled to −60°C in a dry ice-acetone bath. The combined filtrates are evaporated to dryness under reduced pressure, at a temperature below 0°C, obtaining (2'α-hydroxy-3'α,4'α-diacetoxy-5'β-formylcyclopent-1'α-yl)-acetic acid 1,2'-lactone as a homogeneous oil.

EXAMPLE 3

A. Preparation of dimethyl 2-oxoheptylphosphonate. A solution of 100 g. of dimethyl methylphosphonate in 670 ml. of anhydrous tetrahydrofuran is cooled to −78°C under an argon atmosphere. To the cold solution are added dropwise under stirring and under argon atmosphere, 495 ml. of a 0.1M solution of n-butyllithium in tetrahydrofuran, maintaining the temperature at −70°C. When the addition is complete, the reaction mixture is maintained under the same conditions for ten additional minutes, a solution of 58 ml. of methyl caproate dissolved in 187 ml. of tetrahydrofuran is then carefully added, maintaining the temperature at −78°C. The reaction mixture is stirred at −78°C for 2 hours, followed by stirring for 4 hours at room temperature. The excess base is neutralized with acetic acid and the solvent is evaporated under high vacuo. The residue is dissolved in ether-water (1:1, 950 ml. each), the ethereal phase is separated, washed with water and dried over magnesium sulfate. The ether is evaporated and the residue is purified by vacuum distillation, thus obtaining the pure dimethyl 2-oxoheptylphosphonate.

B. To a suspension of 101 mg. of sodium hydride (previously washed with pentane, under argon) in 30 ml. of dimethoxyethane, freshly distilled from lithium aluminum hydride, is added, under stirring and under an atmosphere of argon, a solution of 410 mg. of dimethyl 2-oxoheptylphosphonate in 5 ml. of anhydrous dimethoxyethane. The reaction mixture is stirred for 30 minutes at room temperature an 500 mg. of (2'α-hydroxy-3'α,4'α-diacetoxy-5'β-formylcyclopent-1'α-yl)-acetic acid 1,2'-lactone dissolved in 10 ml. of dimethoxyethane are added. The reaction mixture is stirred at room temperature for 2 hours further, it is then carefully neutralized with acetic acid (to pH 7) and evaporated to dryness under reduced pressure at a temperature below 30°C. The solid residue is purified by chromatography on alkaline alumina, using chloroform-acetone (90:10) as eluant, to obtain [2'α-hydroxy-3'α,4'α-diacetoxy-5'β-(3''-oxo-oct-1''(t)-en-1'' -yl)-cyclopent-1'α-yl]-acetic acid 1,2'-lactone, [2'α-hydroxy-3'α-acetoxy-5'β-(3''-oxo-oct-1''(t)-en-1''-yl)-cyclopent-4'-en-1'α-yl]-acetic acid 1,2'-lactone, and a small amount of dimethyl 2-oxoheptylphosphonate.

EXAMPLE 4

To a stirred solution of 1 g. of [2'α-hydroxy-3'α-acetoxy-5'β-(3''-oxo-oct-1''(t)-en-1''-yl)-cyclopent-4'-en-1'α-yl]-acetic acid 1,2'-lactone in 10 ml. of dimethoxyethane, freshly distilled from lithium aluminum hydride are added 5 ml. of zinc borohydride reagent in anhydrous dimethoxyethane. The reaction mixture is stirred for an additional hour at room temperature, and treated with a saturated solution of sodium bitartrate until the evolution of gas ceases. It is then diluted with methylene chloride, dried over magnesium sulfate and evaporated to dryness under vacuo at a temperature below 30°C, to yield [2'α-hydroxy-3'α-acetoxy-5'β-(3''α-hydroxyoct-1''(t)-en-1'''-yl)-cyclopent-4'-en-1'α-yl]-acetic acid 1,2'-lactone in mixture with the 3''α-hydroxy isomer.

This oily mixture is separated into the individual isomers by thin-layer chromatography using a mixture of methylene chloride-acetone (75:25) as eluant.

The zinc borohydride reagent is prepared from 0.025 mol of fused zinc chloride, 0.050 mol of sodium borohydride in 50 ml. of dimethoxyethane, stirring the mixture for 16 hours and filtering the insoluble material under argon atmosphere.

EXAMPLE 5

A solution of 2.8 g. of [2'α-hydroxy-3'α-acetoxy-5'β-(3''α-hydroxyoct-1''(t)-en-1''-yl)-cyclopent-4'-en-1'α-yl]-acetic acid 1,2'-lactone in 45 ml. of methanol is treated with 1.255 g. of anhydrous potassium carbonate, and the reaction mixture stirred for 1 hour at room temperature. It is then cooled to 0°C and neutralized with 10% aqueous hydrochloric acid, until a pH of 2 to 3 is obtained. Ethyl acetate is added and the organic solution washed with water to neutral, dried over magnesium sulfate and evaporated to dryness under vacuo, to yield 500 mg. of [2'α,3'α-dihydroxy-5'β-(3''α-hydroxyoct-1''(t)-en-1''-yl)-cyclopent-4'-en-1'α-yl]-acetic acid 1,2'-lactone which can be purified by thin-layer chromatography.

EXAMPLE 6

To a solution of 1.4 g. of [2'α-hydroxy-3'α-acetoxy-5'β-(3''β-hydroxyoct-1''(t)-en-1''-yl)-cyclopent-4'-en-1'α-yl]-acetic acid 1,2'-lactone in 85 ml. of anhydrous tetrahydrofuran are added 3.2 g. of manganese dioxide, and the reaction mixture is stirred for 30 minutes at room temperature; 3.2 g. portions of manganese dioxide are added at 30 minute intervals, repeating this operation for seven times. The manganese dioxide is separated by filtration, washing carefully this solid material with hot acetone. The combined organic filtrates are evaporated to dryness under reduced pressure, and the residue is purified by thin-layer chromatography obtaining the pure (2'α-hydroxy-3'α-acetoxy-5'β-(3''-oxo-oct-1''(t)-en-1''-yl)-cyclopent-4'-en-1'α-yl)-acetic acid 1,2'-lactone, identical to the product obtained in Example 3.

EXAMPLE 7

To a solution of 2 g. of [2'α,3'α-dihydroxy-5'β-(3''α-hydroxyoct-1''(t)-en-1''-yl)-cyclopent-4'-en-1'α-yl]-acetic acid 1,2'-lactone in 20 ml. of methylene chloride are added 20 mg. of p-toluenesulfonic acid and 2 ml. of freshly distilled dihydropyran. The reaction mixture is stirred for 15 minutes, at room temperature, a few drops of pyridine are added and diluted with ether. The ethereal solution is washed with 100 ml. of 50% aqueous sodium chloride solution and then with saturated sodium chloride solution. The organic phase is separated, dried over magnesium sulfate and evaporated to dryness under reduced pressure, at approximately 0°C. The oily residue is purified by thin-layer chromatography using chloroform-methanol 9:1 as eluant, to produce the pure [2'α-hydroxy-3'α-tetrahydropyranyloxy-5'β-(3''α-tetrahydropyranyloxyoct-1''(t)-en-1''-yl)-cyclopent-4'-en-1'α-yl]-acetic acid 1,2'-lactone.

EXAMPLE 8

One gram of [2'α-hydroxy-3'α-tetrahydropyranyloxy-5'β-(3''α-tetrahydropyranyloxyoct-1''(t)-en-1''-yl)-cyclopent-4'-en1'α-yl]-acetic acid 1,2'-lactone, is dissolved in 20 ml. of anhydrous toluene. The solution is cooled to −60°C and to the cold solution is added a solution of 650 mg. of diisobutylaluminum hydride in 2.7 ml. of anhydrous toluene, stirring the reaction mixture for 15 minutes at −60°C. It is then diluted with methanol until the evolution of gas ceases, the mixture is stirred for 15 minutes further at room temperature and diluted with ether. The organic phase is then separated, washed with saturated sodium chloride solution, dried over magnesium sulfate and evaporated to dryness at about 0°C to produce [2'α-hydroxy-3'α-tetrahydropyranyloxy-5'β-(3'λ'α-tetrahydropyranyloxyoct-1''(t)-en-1''-yl)-cyclopent-4'-en-1'α-yl]-acetaldehyde 1,2'-hemiacetal.

EXAMPLE 9

A stirred suspension of 440 mg. of sodium hydride in 5 ml. of anhydrous dimethylsulfoxide is heated to 80°C for ½ hour under an argon atmosphere. 1.4 Ml. of resulting solution are added to a solution of 380 mg. of dried 5-triphenylphosphoniopentanoic acid bromide in 0.8 ml. of anhydrous dimethylsulfoxide, under an argon atmosphere and under stirring. The reaction mixture is stirred for 5 minutes, 150 mg. of [2'α-hydroxy-3'α-tetrahydropyranyloxy-5'β-(3''α-tetrahydropyranyloxyoct-1''(t)-en-1''-yl)-cyclopent-4'-en-1'α-yl]-acetaldehyde 1,2'-hemiacetal dissolved in 1 ml. of dimethylsulfoxide is added, and the reaction mixture is stirred at room temperature for 18 hours. The solvent is then evaporated under reduced pressure at a temperature below 35°C and the residue is dissolved in 10 ml. of water. The neutral products are extracted with ethyl acetate:ether (1:1) (4 × 4 ml.). The aqeuous phase is acidified with saturated aqueous oxalic acid solution to pH 2, and extracted several times with a mixture of pentane:diethyl ether (1:1). The combined organic extracts are washed with saturated sodium chloride solution, dried over magnesium sulfate and evaporated to dryness at a temperature not higher than 20°C. Purification of the residue by t.l.c. using chloroform:methanol (9:1) as eluant, affords the pure 9α-hydroxy-10α, 15α-bistetrahydropyranyloxyprosta-5-cis,11,13-trans-trienoic acid.

The 5-triphenylphosphoniopentanoic acid bromide used as reagent is prepared by reflux of a mixutre of 9.5 g. of 5-bromopentanoic acid, 14.4 g. of triphenylphosphine and 100 ml. of acetonitrile for about 70 hours. The insoluble material is separated by filtration and the filtrate is concentrated to a small volume. The product is crystallized by addition of ether, and is further purified by two subsequent recrystallizations from acetonitrile-ether.

EXAMPLE 10

A mixture of 173 mg. of 9α-hydroxy-10α,15α-bistetrahydropyranyloxyprosta-5-cis,11,13-trans-trienoic acid, 0.45 ml. of tetrahydrofuran and 4.5 ml. of 65% aqueous acetic acid is stirred at 40°C for 4 hours, cooled to 0°C and evaporated to dryness under reduced pressure; the oily residue is purified by t.l.c. using chloroform:methanol (9:1) as eluant, thus yielding the pure 9α,10α,15α-trihydroxyprosta-5-cis,11,13-trans-trienoic acid (10α-hydroxy-11-desoxy-11-dehydro-$PGF_{2\alpha}$).

In another experiment the reaction mixture is kept at room temperature for 18 hours, obtaining the same results.

EXAMPLE 11

To a solution of 100 mg. of 9α-hydroxy-10α,15α-bistetrahydropyranyloxyprosta-5-cis,11,13-trans-trienoic acid in 10 ml. of methanol is added a solution of 50 mg. of oxalic acid in 1 ml. of water, and the reaction mixture is maintained at room temperature for 1 hour. It is then diluted with water and extracted with methylene chloride. The organic extract is washed with sodium chloride solution, dried over magnesium sulfate and evaporated to dryness under reduced pressure. The oily residue is purified by t.l.c. using chloroform:methanol (9:1) as eluant, thus yielding the pure 9α,10α,15α-trihydroxyprosta-5-cis,11,13-trans-trienoic acid, identical to the obtained in the foregoing Example.

EXAMPLE 12

A solution of 100 mg. of 9α-hydroxy-10α,15α-bistetrahydropyranyloxyprosta-5-cis,11,13-trans-trienoic acid in 4 ml. of purified acetone is cooled to −10°C and treated under an atmosphere of nitrogen and with stirring, with 0.15 ml. of an 8N solution of chromic acid (prepared by mixing 26 g. of chromium trioxide with 23 ml. of concentrated sulfuric acid and diluting with water to 100 ml.). The reaction mixture is stirred for 30 minutes further at −10°C, 0.15 ml. of isopropanol are then added to destroy the excess reagent, and the mixture diluted with ethyl acetate. The solution is immediately washed three times with sodium chloride solution, dried over magnesium sulfate and evaporated to dryness under reduced pressure, to give 9-keto-10α,15α-bistetrahydropyranyloxyprosta-5-cis,11,13-trans-trienoic acid, which is purified by t.l.c. using chloroform-methanol (9:1) as eluant.

Upon cleavage of the tetrahydropyranyloxy moiety with acetic acid-water (65:35), in accordance with the method of Example 10 there is obtained 9-keto-10α,1-5α-dihydroxyprosta5-cis,11,13-trans-trienoic acid (10α-hydroxy-11-desoxy-11-dehydro-$PGE_2$).

EXAMPLE 13

To a suspension of 50 g. of diatomaceous earth (dried for 24 hours at 105°C) and 45.2 g. of chromium trioxide-dipyridine complex in 500 ml. of anhydrous methylene chloride, cooled to 0° to 2°C are added, under stirring, 5 g. of (2'α-hydroxy-3'α,4'α-diacetoxy-5'β-hydroxymethylcyclopent-1'α-yl)-acetic acid 1,2'-lactone dissolved in 500 ml. of methylene chloride and the mixture is stirred for ten minutes further, maintaining the temperature at about 0°C; 90 g. of sodium bisulfate are then added and the mixture is stirred for an additional 10 minute period, the solids are separated by filtration and washed well with ethyl acetate. To the combined filtrates are added 5 g. of sodium carbonate, and the mixture is stirred for 15 minutes, the solid material is filtered off and washed well with ethyl acetate, the combined filtrates are washed with water, dried over magnesium sulfate and evaporated to dryness in vacuo, at about 0°C to yield 2'α-hydroxy-3'α-acetoxy-5'β-formylcyclopent-4'-en-1'α-yl)-acetic acid 1,2'-lactone as a homogeneous oil.

EXAMPLE 14

To a prehydrogenated suspension of 300 mg. of 5% palladium charcoal catalyst in 20 ml. of dimethoxyethane is added a solution of 500 mg. of (2'α-hdyroxy-3'α-acetoxy-5'β-formylcyclopent-4'en-1'α-yl)-acetic acid 1,2'-lactone, in 40 ml. of dimethoxyethane, and the mixture is stirred under hydrogen atmosphere until the absorption of hydrogen ceases. The catalyst is then separated by filtration and washed well with ethyl acetate. The combine organic filtrates are evaporated to dryness, to yield (2'α-hydroxy-3'α-acetoxy-5'β-formylcyclopent-1'α-yl)-acetic acid 1,2'-lactone, which can be purified by thin-layer chromatography using benzene-dioxane 90:10 as gradient.

EXAMPLE 15

To a suspension of 0.476 g. of sodium hydride (previously washed with pentane, under argon) in 112 ml. of dimethoxyethane freshly distilled from lithium aluminum hydride is added, under stirring and under an atmosphere of argon, a solution of 3.5 g. of dimethyl 2-oxoheptyl phosphonate, prepared as described in Example 3, in 41 ml. of anhydrous dimethoxyethane. The reaction mixture is stirred for 30 minutes at room temperature and 1.4 g. of (2'α-hydroxy-3'α-acetoxy-5'β-formylcyclopent-1'α-yl)-acetic acid 1,2'-lactone dissolved in 40 ml. of dimethoxyethane are added. The reaction mixture is stirred at room temperature for 2 hours further, it is then carefully neutralized with acetic acid (to pH 7) and evaporated to dryness under reduced pressure at a temperature below 30°C. The residue is dissolved in methylene chloride and filtered through Celite, diatomaceous earth. The filtrate is evaporated to dryness under reduced pressure, and the residue purified by chromatography using an 80 × 20 cm silica plate and a methylene chloride-ethyl acetate (80:20) mixture as eluant, to obtain [2'α-hydroxy-3'α-acetoxy-5'β-(3''-oxo-oct-1''(t)-en-1''-yl)-cyclopent-1'α-yl]-acetic acid 1,2'-lactone, in pure form.

EXAMPLE 16

To a stirred solution of 330 mg. of [2'α-hydroxy-3'α-acetoxy-5'β-(3''-oxo-oct-1''(t)-en-1''-yl)-cyclopent-1'α-yl]-acetic acid 1,2'-lactone in 3 ml. of dimethoxyethane freshly distilled from lithium aluminum hydride are added 0.6 ml. of freshly prepared zinc borohydride reagent, prepared as described in Example 4, in anhydrous dimethoxyethane. The reaction mixture is stirred for 90 minutes at room temperature, and treated with a saturated solution of sodium potassium tartrate until the evolution of gas ceases. It is then diluted with methylene chloride, dried over magnesium sulfate and evaporated to dryness under vacuo at a temperature below 30°C, to yield [2'α-hydroxy-3'α-acetoxy-5'β-(3''α-hydroxyoct-1''(t)-en-1''-yl)-cyclopent-1'α-yl]-acetic acid 1,2'-lactone in mixture with the 3''β-hydroxy isomer.

This oily mixture is separated into the individual isomers by t.l.c. using a mixture of methylene chloride-ether (70:30) as eluant.

EXAMPLE 17

A solution of 260 mg. of [2'α-hydroxy-3'α-acetoxy-5'β-(3''α-hydroxyoct-1''(t)-en-1''-yl)-cyclopent-1'α-yl]-acetic acid 1,2'-lactone in 3.4 ml. of methanol is treated with 117 mg. of anhydrous potassium carbonate, and the reaction mixture stirred for 1 hour at room temperature. It is then cooled to 0°C and neutralized with 10% aqueous hydrochloric acid, until a pH of 2 to 3 is obtained. Ethyl acetate is added and the organic solution washed with saturated sodium potassium tartrate solution, dried over magnesium sulfate and evaporated to dryness under vacuo, to yield [2'α,3'α-dihydroxy-5'β-(3''α-hydroxyoct-1''(t)-en-1''-yl)-cyclopent-1'α-yl]-acetic acid 1,2'-lactone.

EXAMPLE 18

To a solution of 1.65 g. of [2'α,3'α-dihydroxy-5'β-(3''α-hydroxyoct-1''(t)-en-1''-yl)-cyclopent-1'α-yl]-acetic acid 1,2'-lactone in 16.5 ml. of methylene chloride are added 16.5 mg. of p-toluenesulfonic acid, and moisture is eliminated by azeotropic distillation with tetrahydrofuran-toluene (three times). The mixture is cooled to room temperature and treated with 1.65 ml. of freshly distilled dihydropyran. The reaction mixture is stirred for 15 minutes, at room temperature, a few drops of pyridine are added and diluted with ether. The ethereal solution is washed with 100 ml. of 50% aqueous sodium chloride solution and then with saturated sodium chloride solution. The organic phase is separated, dried over magnesium sulfate and evaporated to dryness under reduced pressure, at approximately 0°C. The oily residue is purified by t.l.c. using chloroform-methanol 9:1 as eluant, to produce the pure [2'α-hydroxy-3'α-tetrahydropyranyloxy-5'β-(3''α-tetrahydropyranyloxyoct-1''(t)-en-1''-yl)-cyclopent-1'α-yl]-acetic acid 1,2'-lactone.

EXAMPLE 19

A solution of 384 mg. of [2'α-hydroxy-3'α-tetrahydropyranyloxy-5'β-(3''α-tetrahydropyranyloxyoct-1''(t)-en-1''-yl)-cyclopent-1'α-yl]-acetic acid 1,2'-lactone dissolved in 7.7 ml. of anhydrous toluene is cooled to −60°C and to the cold solution is added dropwise a solution of 250 mg. of diisobutylaluminum hydride in 1.25 ml. of anhydrous toluene, stirring the reaction mixture for 30 minutes at −60°C. It is then diluted with methanol until the evolution of gas ceases. The mixture is stirred for 15 minutes further at room temperature and diluted with ether. The organic phase is then separated, washed with saturated sodium chloride solution, dried over magnesium sulfate and evaporated to dryness at about 0°C to produce [2'α-hydroxy-3'α-tetrahydropyranyloxy-5'β-(3''α-tetrahydropyranyloxyoct-1''(t)-en-1''-yl)-cyclopent-1'α-yl]-acetaldehyde 1,2'-hemiacetal.

EXAMPLE 20

A stirred suspension of 440 mg. of sodium hydride (previously washed with hexane distilled from phosphorous pentoxide) in 5 ml. of anhydrous dimethylsulfoxide is heated to 80°C for ½ hour under an argon atmosphere; 0.324 ml. of the resulting solution are added to a solution of 151 mg. of dried 5-triphenylphosphoniopentanoic acid bromide in 0.4 ml. of anhydrous dimethylsulfoxide, under an argon atmosphere and under stirring. The reaction mixture is stirred for five minutes, 60 mg. of [2'α-hydroxy-3'α-tetrahydropyranyloxy-5'β-(3''α-tetrahydropyranyloxyoct-1''(t)-en-1''-yl)-cyclopent-1'α-yl]-acetaldehyde 1,2'-hemiacetal dissolved in 0.5 ml. of dimethylsulfoxide is added, and the reaction mixture is stirred at room temperature for 18 hours. The solvent is then evaporated under reduced pressure at a temperature below 35°C and the residue is dissolved in 10 ml. of water. The neutral products are extracted with ethyl acetate:ether (1:1) (4 × 4 ml.). The aqueous phase is acidified with saturated aqueous oxalic acid solution to pH 2, and extracted several times with a mixture of pentane:ether (1:1). The combined organic extracts are washed with saturated sodium chloride solution, dried over magnesium sulfate and evaporated to dryness at a temperature not higher than 20°C. Purification of the residue by t.l.c. using chloroform:methanol 9:1 as eluant, affords the pure 9α-hydroxy-10α,15α-bistetrahydropyranyloxyprosta-5-cis,13-trans-dienoic acid.

A mixture of 70 mg. of 9α-hydroxy-10α,15α-bistetrahydropyranyloxyprosta-5-cis,13-trans-dienoic acid and 1.8 ml. of 65% aqeuous acetic acid is stirred at 40°C for 4 hours, cooled to 0°C and evaporated to dryness under reduced pressure; the oily residue is purified by t.l.c. using chloroform:methanol (9:1) as eluant, thus yielding the pure 9α,10α,15α-trihydroxyprosta-5-cis,13-trans-dienoic acid.

EXAMPLE 21

A solution of 40 mg. of 9α-hydroxy-10α,15α-bistetrahydropyranyloxyprosta-5-cis,13-trans-dienoic acid in 1 ml. of purified acetone is cooled to −10°C and treated under an atmosphere of nitrogen and with stirring, with 0.1 ml. of an 8N solution of chromic acid (prepared by mixing 26 g. of chromium trioxide with 23 ml. of concentrated sulfuric acid and diluting with water to 100 ml.). The reaction mixture is stirred for 1 hour further at −10°C, 0.1 ml. of isopropanol is then added to destroy the excess reagent, and the mixture diluted with 6 ml. of ethyl acetate. The solution is immediately washed three times with sodium chloride solution, dried over magnesium sulfate and evaporated to dryness under reduced pressure, to give 9-keto-10α,15α-bistetrahydropyranyloxyprosta-5-cis,13-trans-dienoic acid, which is purified by t.l.c. using chloroform-methanol (9:1) as eluant.

Upon cleavage of the tetrahydropyranyloxy moiety with acetic acid-water (65:35), in accordance with the method of Example 10, there is obtained 9-keto-10α,15α-dihydroxyprosta-5-cis,13-trans-dienoic acid.

EXAMPLE 22

Fifteen milligrams of 9-keto-10α,15α-dihyroxyprosta-5-cis,13-trans-dienoic acid is dissolved in a mixture of 2 ml. of benzene and 3 ml. of acetone containing 5 mg. of freshly prepared tris-(triphenylphosphine)-chlororhodium, at room temperature. The resulting mixture is stirred in a hydrogen atmosphere and aliquots are removed at periodic intervals. The aliquots are esterified with diazomethane and analyzed by gas liquid chromatography to determine whether hydrogenation has been completed. When the hydrogenation is determined to be essentially complete (ca. 6 hours) the reaction mixture is applied to 20% wt. silver nitrate impregnated silica gel (G) preparative plates developing with chloroform:methanol:acetic acid:water in a 95:71:1:0.6 parts by volume ratio. The zone corresponding to the 9-keto-10α,11α-dihydroxyprost-13-trans-enoic acid is eluted with a 90:10 by vol., ratio mixture of chloroform and methanol yielding pure 9-keto-10α,15α-dihydroxyprost-13-trans-enoic acid.

Similarly by following the same procedure but respectively using the corresponding 5-cis olefin prostaglandin derivative as starting materials, the following compounds are respectively prepared:
9α,10α,15α-trihydroxyprost-13-trans-enoic acid;
9-keto-10α,15α-dihydroxyprosta-11,13-trans-dienoic acid; and
9α,10α,15α-trihydroxyprosta-11,13-trans-dienoic acid.

EXAMPLE 23

To a solution of 100 mg. of 9α,10α,15α-trihydroxyprosta-5-cis,11,13-trans-trienoic acid in 5 ml. of ether is added 1 ml. of an ethereal solution of diazomethane, and the reaction mixture is maintained at room temperature for 10 minutes. The solvents and excess reagent are eliminated by vacuum distillation and the residue is purified by t.l.c. to afford 9α,10α,15α-trihydroxyprosta-5-cis,11,13-trans-trienoic acid methyl ester.

In a similar manner but using diazoethane in place of diazomethane, the ethyl ester of 9α,10α,15α-trihydroxyprosta5-cis,11,13-trans-trienoic acid is obtained.

Likewise 9α,10α,15α-trihydroxyprosta-5-cis,13-trans-dienoic acid, 9-keto-10α,15α-dihydroxyprosta-5-cis,11,13-trans-trienoic acid and 9-keto-10α,15α-dihydroxyprosta-5-cis,13-trans-dienoic acid are converted into the corresponding methyl and ethyl esters.

Similarly the corresponding methyl and ethyl esters of the products of Example 22 are respectively prepared.

EXAMPLE 24

A mixture of 100 mg. of 9α,10α,15α-trihydroxyprosta-5-cis,11,13-trans-trienoic acid, 0.4 ml. of pyridine and 0.8 ml. of acetic anhydride is kept at room temperature for 1 hour. The reaction mixture is then evaporated to dryness under reduced pressure and the residue is dissolved in ethyl acetate, 50 mg. of sodium bisulfate are added and the solution is filtered through diatomaceous earth. The filtrate is evaporated to dryness to yield 9α,10α,15α-triacetoxyprosta-5-cis,11,13-trans-trienoic acid.

By the same process but using propionic, caproic and cyclopentylpropionic anhydrides as esterifying agents there are respectively obtained the 9α,10α,15α-tripropionoxy-, 9α,10α15α-tricaproxy- and 9α,10α,15α-tricyclopentylpropionoxy-derivatives of prosta-5-cis,11,13-trans-trienoic acid.

In a similar manner, 9-keto-10α,15α-dihydroxyprosta-5-cis,11,13-trans-trienoic acid and 9-keto-10α,15α-dihydroxyprosta-5-cis,13-trans-dienoic acid and the products of Example 22 are respectively converted into the corresponding diacetates, dipropionates, dicaproates and dicyclopentylpropionates.

EXAMPLE 25

To a solution of 100 mg. of 9-keto-10α,15α-dihydroxyprosta-5-cis,11,13-trans-trienoic acid in 10 ml. of methanol is added 3 ml. of a 0.1N solution of sodium hydroxide, and the mixture is stirred at room temperature for 1 hour. It is then evaporated to dryness under reduced pressure, to give the sodium salt of 9-keto-10α,15α-dihydroxyprosta-5-cis,11,13-trans-trienoic acid.

By employing 1.1 molar equivalents of potassium hydroxide (in the form of a 0.1N solution) in place of sodium hydroxide in the above procedure, the potassium salt of 9-keto-10α,15α-dihydroxyprosta-5-cis,11,13-trans-trienoic acid is obtained.

Similarly, the sodium and potassium salts of the other prostanoic acid derivatives obtained in the previous Examples are produced.

EXAMPLE 26

To a solution of 100 mg. of 9-keto-10α,15α-dihydroxyprosta-5-cis,11,13-trans-trienoic acid in 10 ml. of methanol is added a mixture of 3 ml. of concentrated ammonium hydroxide solution and 5 ml. of methanol. The resulting mixture is stirred for 2 hours at room temperature and then evaporated to dryness, to yield the ammonium salt of 9-keto-10α,15α-dihydroxyprosta-5-cis,11,13-trans-trienoic acid.

By employing dimethylamine, diethylamine or dipropylamine in place of ammonium hydroxide in the above process, the corresponding salts of 9-keto-10α,15α-dihydroxyprosta-5-cis,11,13-trans-trienoic acid are obtained.

In a similar manner, the ammonia, dimethylamine, diethylamine and dipropylamine salts of 9α,10α,15α-trihydroxyprosta-5-cis,11,13 -trans-trienoic acid, 9-keto-10α,15α-dihydroxyprosta-5-cis,13-trans-dienoic acid,; 9α,10α,15α-trihydroxyprosta-5cis,13-trans-dienoic acid and the products of Example 22 are respectively prepared.

EXAMPLE 27

To a solution of 400 mg. of 9α,10α,15α-trihydroxyprosta-5-cis,11,13-trans-trienoic acid in 5 ml. of anhydrous acetone and 2 ml. of 2,2-dimethoxypropane are added 5 mg. of p-toluenesulfonic acid, and the reaction mixture is kept at room temperature for 2.5 hours. A few drops of pyridine are then added, and the solvents eliminated under reduced pressure. The residue is purified by t.l.c., to yield 9α,10α-isopropylidenedioxy-15α-hydroxyprosta-5-cis,11,13-trans-trienoic acid.

In a similar manner but using methyl ethyl ketone, cyclohexanone or acetophenone in place of acetone, there are obtained 9α,10α-isobutylidenedioxy-15α-hydroxyprosta-5-cis,11,13-trans-trienoic acid, the 9,10-cyclohexanonide of 9α,10α,15α-trihydroxyprosta-5-cis,11,13-trans-trienoic acid and the 9,10-acetophenonide of 9α,10α,15α-trihydroxyprosta-5-cis,11,13-trans-trienoic acid, respectively.

Likewise, starting from 9α,10α,15α-trihydroxyprosta-5-cis,13-trans-dienoic acid there are produced:
9α,10α-isopropylidenedioxy-15α-hydroxyprosta-5-cis,13-trans-dienoic acid;
9α,10α-isobutylidenedioxy-15α-hydroxyprosta-5-cis,13-trans-dienoic acid;
9,10-cyclohexanonide of 9α,10α,15α-trihydroxyprosta-5-cis,13-trans-dienoic acid; and
9,10-acetophenonide of 9α,10α,15α-trihydroxyprosta-5-cis,13-trans-dienoic acid.

Similarly by following the same procedure but respectively using the corresponding products of Example 22 as starting materials, the following compounds are respectively prepared:
9α,10α-isopropylidenedioxy-15α-hydroxyprosta-11,13-transdienoic acid;
9α,10α-isobutylidenedioxy-15α-hydroxyprosta-11,13-transdienoic acid;
9α,10α-isopropylidenedioxy-15α-hydroxyprosta-13-transenoic acid;
9α,10α-isobutylidenedioxy-15α-hydroxyprost-13-transenoic acid;
and the 9,10-cyclohexanonides and 9,10-acetophenonides of 9α,10α,15α-trihydroxyprosta-11,13-trans-dienoic acid and 9α,10α,15α-trihydroxyprost-13-trans-enoic acid respectively.

Obviously many modifications and variations of the invention, described herein above and below in the Claims, can be made without departing from the essence and scope thereof.

What is claimed is:

1. A compound selected from the group of those represented by the formula:

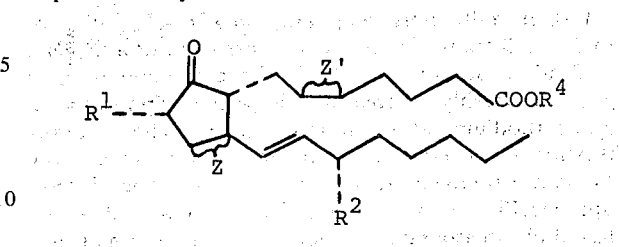

wherein $R^1$ and $R^2$ are independently selected from the group of hydroxy, hydrocarbon carboxylic containing from one to 12 carbon atoms or the group consisting of methoxy, ethoxy, cycopentyloxy, tetrahydrofuran-2-yloxy, tetrahydropyran-2-yloxy and 4-methoxytetrahydropyran-4-yloxy;
$R^4$ is hydrogen or lower alkyl;
Z is a carbon-carbon double bond; and
Z' is a cis-olefin double bond or a saturated linkage; and pharmaceutically acceptable salts where $R^4$ is hydrogen.

2. The compound of claim 1 wherein said compound is selected from the group of 9-keto-10α,15α-dihydroxyprosta-5-cis,11,13-trans-trienoic acid and pharmaceutically acceptable salts thereof.

3. The compound of claim 1 wherein said compound is selected from the group of 9-keto-10α,15α-dihydroxyprosta-11,13-trans-dienoic acid and pharmaceutically acceptable salts thereof.

* * * * *

UNITED STATES PATENT OFFICE
CERTIFICATE OF CORRECTION

Patent No. 3,931,297                    Dated   January 6, 1976

Inventor(s)   Pierre Crabbe

It is certified that error appears in the above-identified patent and that said Letters Patent are hereby corrected as shown below:

Column 1, line 26, "Bergstroms" should read --- Bergström ---.
Column 2, line 49, "are" should read --- as ---.  Column 3, line 1, "perlargonate" should read --- pelargonate ---.  Column 3, line 3, "diethylaclate" should read --- diethylacetate ---.  Column 3, Formula VIII, that portion

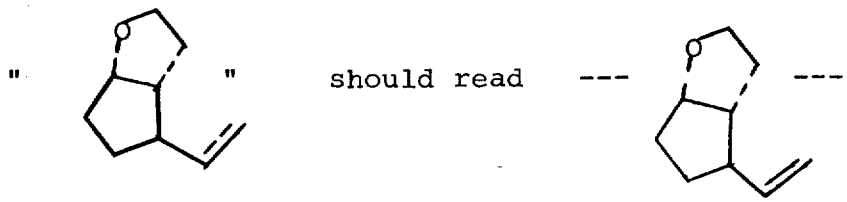

Column 9, line 3, "form" should read --- from ---.  Column 10, line 5, "treatment mild" should read --- treatment under mild ---.
Column 15, line 6, "then excess" should read --- then the excess ---.
Column 15, line 23, "anhydrous -chloroacrylonitrile" should read --- anhydrous α-chloroacrylonitrile ---.  Column 16, line 40, "norbornen5" should read --- norbornen-5 ---.  Column 17, line 53, "orgainc" should read --- organic ---.  Column 20, line 43, "3'λ'α" should read --- 3"α- ---.  Column 21, line 68, Column 22, line 1, "1-5α" should read --- 15α ---.  Column 22, line 1, "dyhydroxyprosta5" should read --- dihydroxyprosta-5 ---.  Column 22, line 29, "hdyroxy" should read --- hydroxy ---.  Column 22, line 64, that portion reading "EXAM-" should be deleted and inserted in Column 21, line 65 so that it reads:

--- EXAMPLE 16 ---.

Column 24, lines 67 and 68, "1-5α" should read --- 15α ---.  Column 25, line 17, "95:71" should read --- 95:75 ---and line 18, "11a" should read --- 15α ---.  Column 25, line 44, "yprosta5" should read --- yprosta-5 ---.  Column 26, line 47, "acid,;" should read --- acid; --- and line 47 "-5cis" should read --- 5-cis ---.

Signed and Sealed this

Sixth Day of July 1976

[SEAL]

Attest:

RUTH C. MASON
Attesting Officer

C. MARSHALL DANN